US008770226B2

(12) United States Patent
Wilen et al.

(10) Patent No.: US 8,770,226 B2
(45) Date of Patent: Jul. 8, 2014

(54) RANDOM ACCESS ROTARY VALVE

(75) Inventors: Anders Wilen, Uppsala (SE); Patrik Kallback, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 622 days.

(21) Appl. No.: 13/123,244

(22) PCT Filed: Nov. 9, 2009

(86) PCT No.: PCT/SE2009/051276
§ 371 (c)(1),
(2), (4) Date: Apr. 8, 2011

(87) PCT Pub. No.: WO2010/056189
PCT Pub. Date: May 20, 2010

(65) Prior Publication Data
US 2011/0240899 A1    Oct. 6, 2011

(30) Foreign Application Priority Data
Nov. 13, 2008   (SE) ...................................... 0802392

(51) Int. Cl.
F16K 11/06    (2006.01)
(52) U.S. Cl.
USPC .................................................... 137/625.46
(58) Field of Classification Search
USPC ........................................ 137/625.46, 625.47
See application file for complete search history.

(56) References Cited

U.S. PATENT DOCUMENTS

| 3,868,970 A | * | 3/1975 | Ayers et al. | 137/625.46 |
| 4,625,569 A | * | 12/1986 | Toei et al. | 73/863.72 |
| 5,105,851 A | | 4/1992 | Fogelman | |

(Continued)

FOREIGN PATENT DOCUMENTS

| JP | 61-061052 A | 3/1986 |
| WO | 2004/088303 | 10/2004 |

(Continued)

OTHER PUBLICATIONS

European 09826369 Search report Mar. 27, 2013.

Primary Examiner — John Fox

(57) ABSTRACT

A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more interconnection paths for selective fluidic interconnection of said valve orifices with respect to the rotor position. Wherein the stator comprises, a main inlet port, a main outlet port, a first component feed port, a first component return port, a second component feed port, a second component return port, and wherein the interconnection paths in the rotor are arranged to: —in a first rotor position interconnect the main inlet port with the main outlet port, —in a second rotor position interconnect the main inlet port with the first component feed port and the first component return port with the main outlet port, —in a third rotor position interconnect the main inlet port with the first component feed port, the first component return port with the second component feed port, and the second component return port with the main outlet port, and —in a fourth rotor position interconnect the main inlet port with the second component feed port and the second component return port with the main outlet port.

9 Claims, 8 Drawing Sheets

(56) References Cited

U.S. PATENT DOCUMENTS

| | | | | |
|---|---|---|---|---|
| 5,601,115 | A | * | 2/1997 | Broerman .................... 137/595 |
| 5,803,117 | A | * | 9/1998 | Olsen et al. .............. 137/625.15 |
| 6,012,487 | A | | 1/2000 | Hauck |
| 6,155,123 | A | | 12/2000 | Bakalyar |
| 6,672,336 | B2 | | 1/2004 | Nichols |

| | | |
|---|---|---|
| 2003/0098076 A1 | 5/2003 | Nichols |

FOREIGN PATENT DOCUMENTS

| | | |
|---|---|---|
| WO | WO 2008/103097 | 8/2008 |
| WO | WO 2008/103098 | 8/2008 |
| WO | WO 2008/140377 | 11/2008 |

* cited by examiner

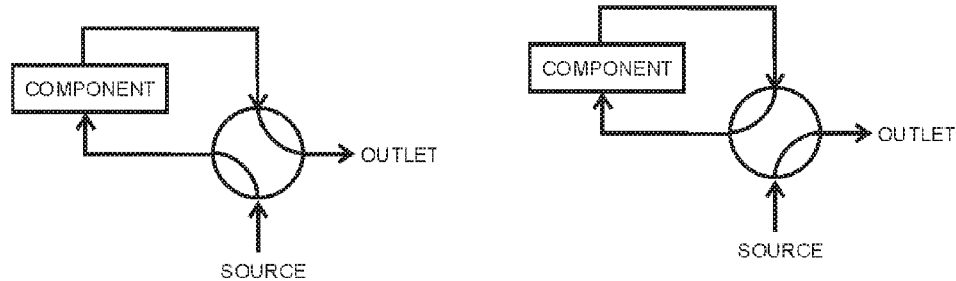
Fig. 1
Prior Art
Fig. 2
Prior Art
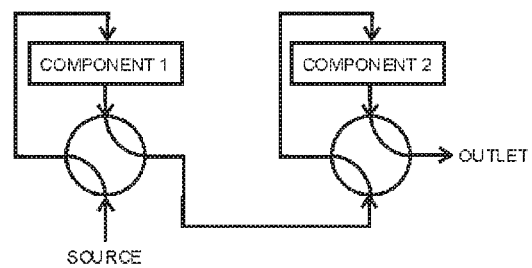
Fig. 3
Prior Art
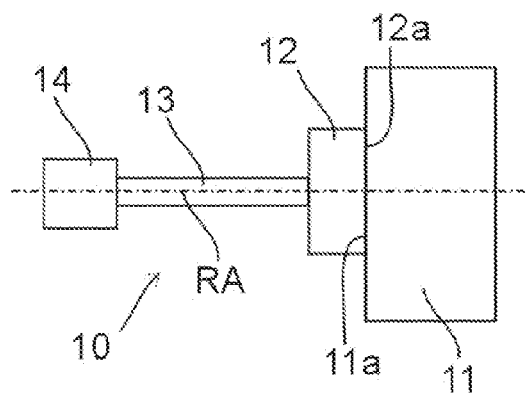
Fig. 4

RANDOM ACCESS ROTARY VALVE

CROSS-REFERENCE TO RELATED APPLICATIONS

This application is a filing under 35 U.S.C. §371 and claims priority to international patent application number PCT/SE2009/051276 filed Nov. 9, 2009, published on May 20, 2010 as WO 2010/056189, which claims priority to application number 0802392-1 filed in Sweden on Nov. 13, 2008.

FIELD OF THE INVENTION

The present invention relates to valves and more specifically to rotary valves for selectively enabling components into a main flow.

BACKGROUND OF THE INVENTION

Valves are commonly used in devices that involve the transportation of a fluid. A typical type of valve, for example used in laboratory systems of moderate sizes, is the rotary valve.

Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotator with respect to the stator.

Rotary valves can be designed to withstand high pressures (such as pressures above 30 MPa). They can be made from a range of materials, such as stainless steel, high performance polymeric materials and ceramics.

The number of inlets/outlets as well as the design of grooves in the rotor or the stator reflects the intended use of a specific valve.

A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

More complicated arrangements, tailor-made to perform one or several specific tasks, are possible. For instance, rotary valves may be used to introduce a fluid sample into the fluid path of an analytical system.

For example, a rotary valve that allows the user to independently of each other control a first flow to either of a set of two outlets, and a second flow to either of a set of another two outlets is described in U.S. Pat. No. 6,672,336 to Nichols.

In many instruments handling a flow of a liquid, such as liquid chromatography systems (LCS), there is sometimes a need to be able to either include or to bypass a component.

This situation is easily solved with a conventional 4-way double-path valve, schematically shown in FIGS. 1 and 2.

FIG. 3 shows two components, each connected to a flow path via a conventional 4-way double-path valve. Thus, one or both of the components can be disconnected from the flow.

However, it would be beneficial to be able to integrate the possibility to disconnect at least one of two components from the flow path into a single valve. One reason for this would be to save cost (e.g. since there is need for one valve motor drive only in the case of an automatically operated valve). Another reason would be the possibility to shorten path lengths by integrating as much paths into the valve as possible, thereby reducing the need for interconnecting tubing.

It would be additionally beneficial if such a valve should include even more functionality, such as the possibility to flush one of the components using a second liquid source. For instance, this would be the case if one of the components requires calibration using a well defined calibration liquid. It would then be useful if this liquid (especially if it is expensive) could be introduced directly (e.g. with a syringe) to the component without the need to have it to pass the entire instrument.

Thus, there is a need for a multipurpose valve that allows at least one of two components to be independently connected to/disconnected from a main flow.

SUMMARY OF THE INVENTION

This is achieved in a valve according to claim 1 of the present application.

Hereby one single rotary valve is achieved which can take at least three different rotary positions, in which either both components are bypassed, only one of the components is connected and the other bypassed or both components are connected to a main flow. This will both give a cheaper valve compared to using two separate valves and minimize interconnecting tubings.

According to one aspect, there is provided a rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more interconnection paths for selective fluidic interconnection of said valve orifices with respect to the rotor position, wherein the stator comprises, a main inlet port, a main outlet port, a first component feed port, a first component return port, a second component feed port, a second component return port, and wherein the interconnection paths in the rotor are arranged to:

in a first rotor position interconnect the main inlet port with the main outlet port, in a second rotor position interconnect the main inlet port with the first component feed port and the first component return port with the main outlet port, in a third rotor position interconnect the main inlet port with the first component feed port, the first component return port with the second component feed port, and the second component return port with the main outlet port, and in a fourth rotor position interconnect the main inlet port with the second component feed port and the second component return port with the main outlet port.

According to one embodiment the valve orifice of the main inlet port is arranged concentric with the rotational axis, the valve orifices of the main outlet port and the first and second component feed ports are angularly distributed at a distance R from the rotational axis, and that the rotor comprises a main inlet interconnection path between the valve orifice of the main inlet port and one point at distance R from the rotational axis.

According to one embodiment the first component feed port is in fluidic contact with the main inlet interconnection path of the rotor at both the second and third rotor position via a stator interconnection channel extending the valve orifice of the first component feed port.

According to one embodiment the valve orifices of the first and second component return ports are angularly distributed at distance R from the rotational axis, and that the rotor comprises two or more transfer interconnection paths for selective pair wise interconnection of the valve orifices arranged at distance R from the rotational axis.

According to one embodiment the valve orifices of the main outlet port, the second component feed port and the first and second component return ports are equidistantly distributed, and that each transfer interconnection path is arranged to interconnect adjacent valve orifices.

According to one embodiment the stator further comprises a secondary inlet port and a secondary outlet port, and wherein the interconnection paths in the rotor are arranged to:

in a fifth rotor position interconnect the secondary inlet port with the second component feed port, and the second component return port with the secondary outlet port. According to one embodiment the valve orifice of the secondary inlet port is arranged at distance R2 from the rotational axis, R≠R2, and the rotor comprises a secondary source interconnection path that is arranged to interconnect the valve orifices of the secondary inlet and the second component feed port when the rotor is in the fifth rotor position, whereas one of the transfer interconnection paths is arranged to interconnect the valve orifices of the second component feed port and the secondary outlet.

According to one embodiment the first rotor position is selected as 0° and the equidistant spacing between adjacent valve orifices is 30°, then the second rotor position is at 90°, the third rotor position is at 120°, the fourth rotor position is at 300°, and the fifth rotor position is at 150°.

According to one embodiment at least one of the first and second components are integrated in the stator in direct communication with the respective ports via interconnection channels in the stator. According to one embodiment the second component in the form of a pH sensor is integrated in the stator.

According to one embodiment there is provided an analytical instrument and a process system comprising a rotary valve according to the present invention.

Suitable embodiments are described in the dependent claims.

BRIEF DESCRIPTION OF THE DRAWINGS

FIG. 1 shows flow through a component using a conventional valve in a first mode.

FIG. 2 shows bypassing the component of FIG. 1 using a conventional valve in a second mode.

FIG. 3 shows two components connected to a flow path using two conventional valves.

FIG. 4 is a schematic side view of a rotary valve.

DETAILED DESCRIPTION OF THE INVENTION

Figure 5:
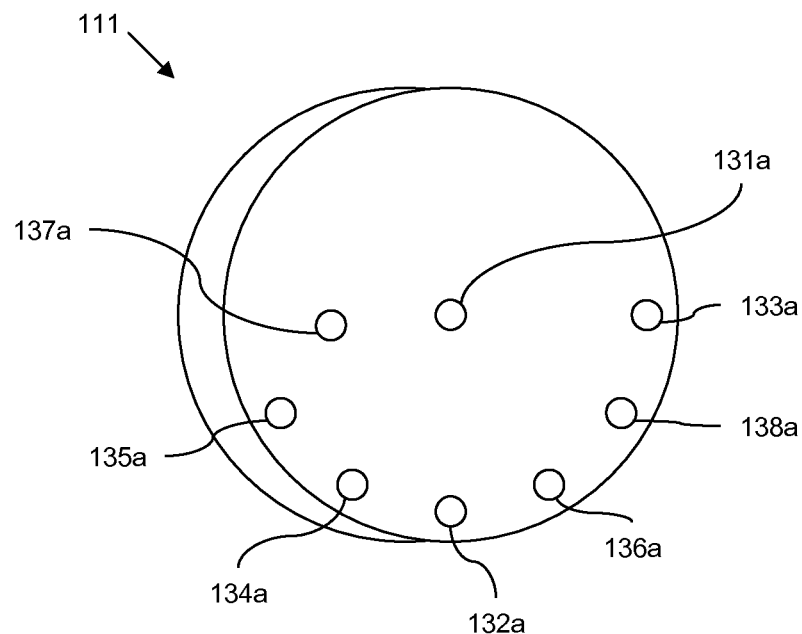
FIG. 5 is a perspective view of a stator of a first embodiment of the invention.

The main parts of a typical rotary valve are schematically shown in FIG. 4 (wherein no brackets or similar load carrying or fastening elements are shown). The rotary valve 10 has a stator 11, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 11, which is fixed with respect to the instrument into which it is built, is provided with ports (not shown in FIG. 4) for fluid communication with a fluid source and any components with which the valve is to co-operate. The ports may be positioned on any suitable part of the stator, and in any suitable direction. The ports are provided with means to connect capillaries or tubing. Such means may be of any suitable type, such as conventional Valco fittings well known to anyone skilled in the art. The ports are via channels in fluid communication with a corresponding set of valve orifices on an inner stator face 11a, i.e. the surface of the stator that during operation is in contact with the rotor 12.

The rotor 12 is typically formed as a disc and has an inner rotor face 12a that is pressed against the flat inner stator face 11a during operation to achieve sealing contact there between. The inner rotor face 12a is provided with one or more interconnection paths which interconnect different valve orifices of the inner stator face 11a depending on the rotary position of the rotor with respect to the stator. The interconnection paths may be any type of path capable of providing fluidic contact between two valve orifices, and may be comprised of an internal channel with discrete orifices, grooves in the inner rotor face or the like.

FIG. 5, which shows a simplified perspective view of the front side of a stator 111, illustrates the inlet and outlet port arrangement for one embodiment of a valve according to the present invention.

Generally, it should be noticed that the angular position of ports, grooves and similar shown in the figures of the present application could differ between different embodiments of the invention, i.e. they could be turned with respect to the rotary axis of the valve, mirrored or altered in other ways as long as their mutual co-operation is still according to the inventive idea.

In addition, since the inlet/outlet ports are connected to orifices on the inner stator face 11a via bores (or any type of channels) it is possible to arrange the ports in a way that differs from the pattern on the inner stator face 11a by making non-linear channels between the ports and the orifices. However, for reasons of simplicity, the ports are shown as being positioned in-line with the inner stator face orifices, as will be described below in relation to FIG. 6.

Thus, the stator 111 of the disclosed embodiment has eight ports 131a-137a that are used to connect the valve to all desired operative components of the instrument.

A main inlet port 131a is a central port used as inlet port from a first liquid source of the instrument, such as a pump, typically via a set of components of the instrument such as detectors, other valves etc., and any connected components such as a chromatography column. A main outlet port 132a serves as an outlet port from which the liquid is allowed to exit to the remaining part of the instrument or out from the instrument. In alternative embodiments, the main inlet port may be a circular or arced groove that is concentric with the rotation axis RA, or it may be comprised of a plurality of discrete valve orifices.

A first component, such as a conductivity monitor or a flow restrictor device, is connectable to the valve via a first component feed port 133a and a first component return port 134a, whereby the feed port 133a acts as an outlet from the valve and the return port 134a as an inlet to the valve for the returning flow from the first component.

A second component, such as a pH monitoring sensor or the like, is connectable to the valve via a second component feed port 135a and a second component return port 136a whereby the feed port 135a acts as an outlet from the valve and the return port 136a as an inlet to the valve for the returning flow from the second component.

According to one embodiment, there is a secondary inlet port 137a that allows a second fluid source (such as a syringe, not shown) to be connected to the valve and to be selectively distributed to at least one of the first and second components. A second fluid source may for instance, be a source of fluid for calibration or manual flushing of one or both of the first and second components by feeding a specific calibration or flushing fluid thereto, as is shown below. The fluid from the second fluid source may be directed to the main outlet port 132a or, in accordance with one embodiment to a secondary outlet port 138a whereby the second fluid is directed to a dedicated flow path. The secondary outlet port 138a may be connected to an alternative flow path in the instrument, e.g. to a waste receptor. It should be noted that both the secondary inlet port 137a and the secondary outlet port 138a are optional, i.e. either one could be omitted if the calibration or flushing is not of interest.

Figure 6:
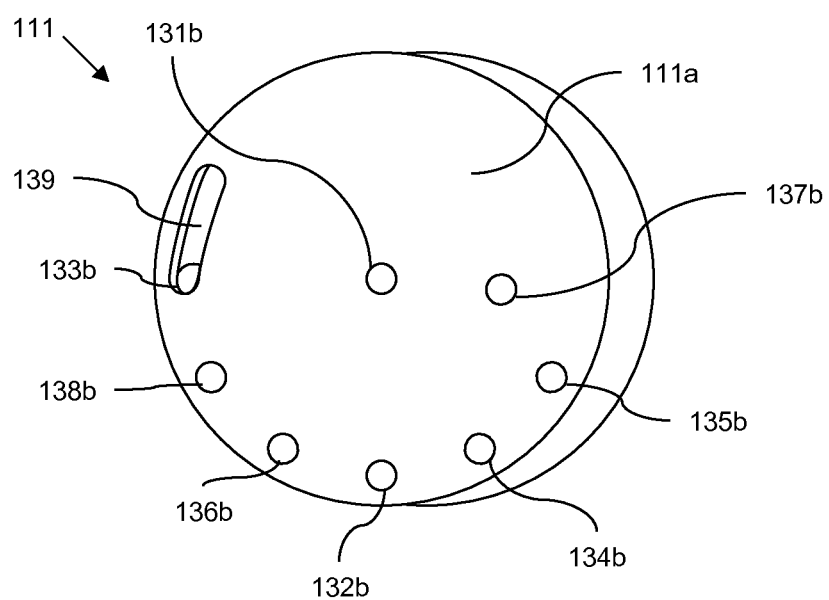
FIG. 6 shows the stator of FIG. 5 from the inner stator face side.

FIG. 6 is a perspective view of the stator 111 of FIG. 5 viewed from the other side, i.e. the inner stator face side 111a. Note that each port is connected to the inner stator face 111a via a channel ending in a corresponding orifice, a main inlet valve orifice 131b, a main outlet valve orifice 132b, a first component feed valve orifice 133b, a first component feed valve orifice 134b, a second component feed valve orifice 135b, a second component return valve orifice 136b, a secondary inlet valve orifice 137b, and a secondary outlet valve orifice 138b shown in FIG. 6. In alternative embodiments, the main inlet valve orifice 131b may be a circular or arced groove that is concentric with the rotation axis RA, or it may be comprised of one or more of discrete valve orifices not arranged concentric with the rotation axis RA.

In order to provide fluidic communication with the first component feed port 133a at more than one rotor position, said port 133a is in communication with a stator interconnection channel that extends between two angular positions at radius R. In the disclosed embodiment, the stator interconnection channel is shown in the form of a stator groove 139 provided in the inner stator face 111a. The groove is typically of essentially the same width as an orifice diameter. The valve orifice 133b is situated inside the stator groove 138.

Figure 7:
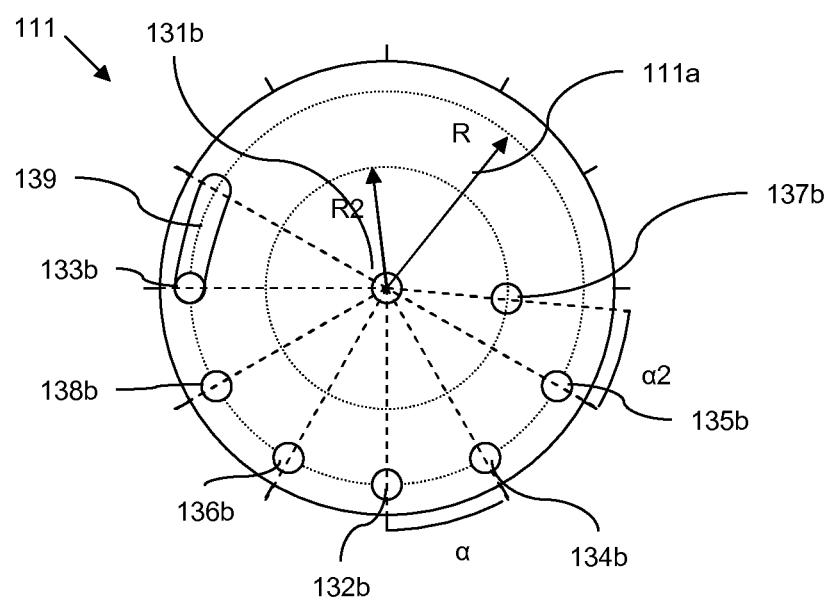
FIG. 7 illustrates the angular distribution of the orifices in the inner stator face of the stator according to FIG. 5

Looking at the inner stator face 111a, the general angular distribution of the orifices and the groove ends is illustrated in FIG. 7. The positions for valve orifices, groove ends (and not used positions) are equally distributed around the center of the stator (which center coincides with the rotary axis of the valve). As described above the positions of the orifices and the partition angle there between can be varied without departing from the inventive idea. Since there are twelve such positions on the stator according to the embodiment, the partition angle $\alpha$ is 30°. All positions but the secondary inlet valve orifice 137b are placed with essentially the same radial distance R to the rotational axis of the valve, whereas the secondary inlet valve orifice 137b is placed at a radius R2 which is different from R. In FIG. 7 the secondary inlet valve orifice 137b is for illustrative reasons placed at a partition angle $\alpha 2$ that is different from $\alpha$, but it should be noted that the angle $\alpha 2$ may be any suitable angle including $\alpha$.

Figure 8:
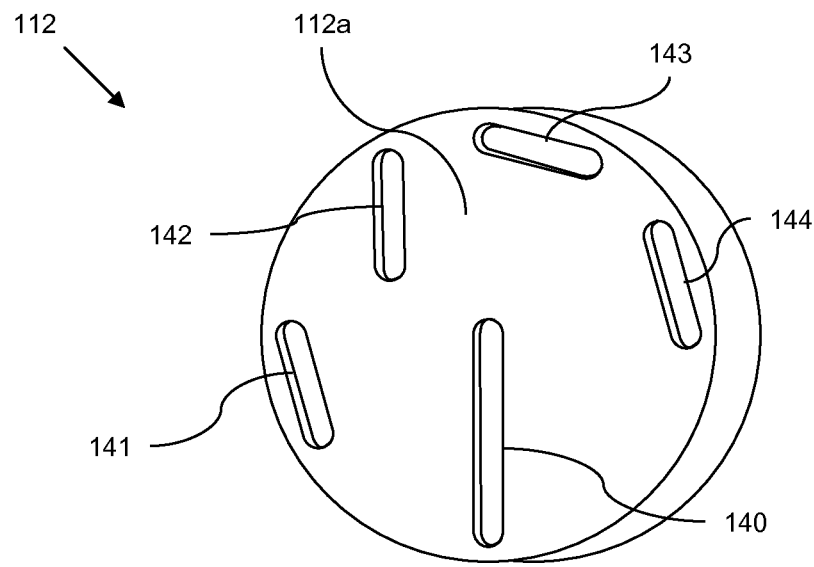
FIG. 8 is a perspective view of a rotor of the first embodiment of the invention from the rotor inner face.

One embodiment of an inner rotor face 112a of a rotor 112 for cooperation with the stator 111 above is shown in FIG. 8. It is provided with five interconnection paths for selective fluidic interconnection of the valve orifices in the inner stator face 111a with respect to the rotor position in the form of grooves in the inner rotor face 112a. A main inlet groove 140 is arranged to provide a main inlet interconnection path between the valve orifice 131b of the main inlet port and a point at distance R from the rotational axis. In order to receive fluid from the main inlet groove, the valve orifices of the main outlet port 132b and the first and second component feed ports 133b and 135b, respectively, are angularly distributed at a distance R from the rotational axis.

Figure 9:
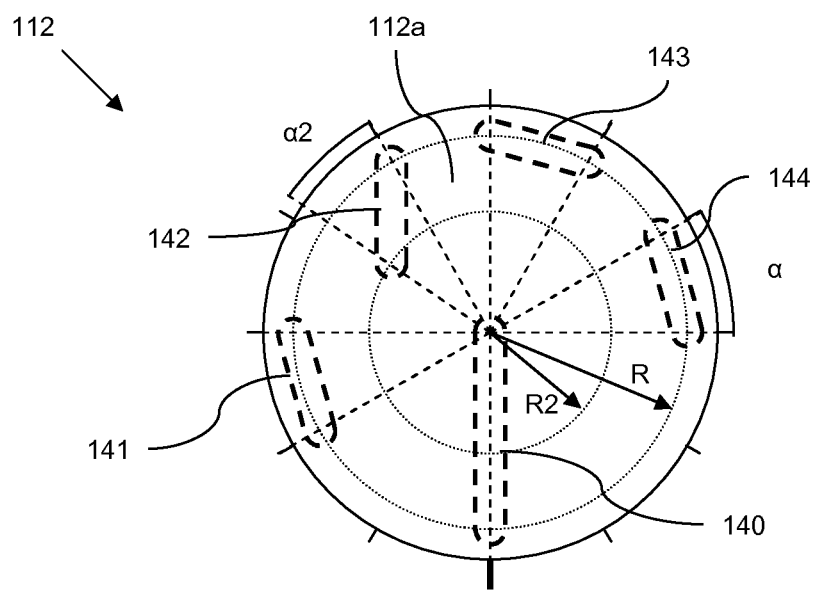
FIG. 9 illustrates the angular distribution of grooves of the inner rotor face of the rotor according to FIG. 8.

As is disclosed in FIG. 7, in the disclosed embodiment, the valve orifices of the first and second component return ports 133b, 134b, 135b, and 136b are angularly distributed at distance R from the rotational axis, and as is disclosed in FIG. 8 the rotor comprises three transfer interconnection paths 141, 143 and 144 for selective pair wise interconnection of the valve orifices arranged at distance R from the rotational axis. In the disclosed embodiment, the valve orifices of the main outlet port 132b, the second component feed port 135b and the first and second component return ports 134b and 136b respectively are equidistantly distributed, and each transfer interconnection path 141, 143, 144 is arranged to interconnect two adjacent valve orifices of said valve orifices. Hence, the transfer interconnection paths 141, 143, 144 each extend over an angle $\alpha$. The angle $\alpha$ is in the present embodiment 30°. The rotor further comprises a secondary source interconnection path in the form of a secondary feed groove 142 that is arranged to interconnect the valve orifices of the second component feed port 137b and the secondary inlet 135b. The mutual positions and shapes of the grooves are more clearly illustrated in FIG. 9.

When assembled, the inner rotor face 112a is pressed against the inner stator face 111a in a manner that is typical for any conventional rotary valve (which is well known for anyone skilled in the art, and will not be explained herein). Depending on the mutual angular positions of the rotor 112 and the stator 111 different operation modes are obtained for the valve. These are illustrated in FIGS. 10a to 10e, wherein the interconnection grooves of the rotor are schematically indicated by thick broken lines, and the fluid flow in the valve by a wave pattern.

Figure 10A:
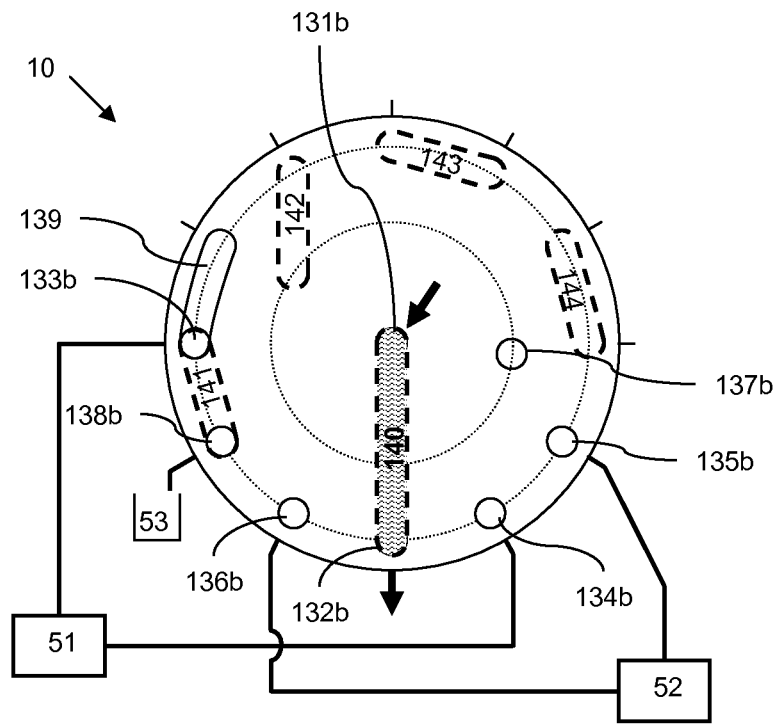
FIGS. 10a to 10e is a schematic view of an embodiment of the invention with the rotor positioned at different rotor positions.

In the first rotor position, as shown in FIG. 10a, the valve is arranged to bypass both a first component 51 and a second component 52. The fluid flow enters the first port 131a, goes via the first orifice 131b through the first rotor groove 121 and exits the valve through the second port 132a (via the second orifice 132b). The other ports and grooves of the valve are not active in the first rotor position, i.e. both the first and the second components 51, 52 are bypassed.

Figure 10B:
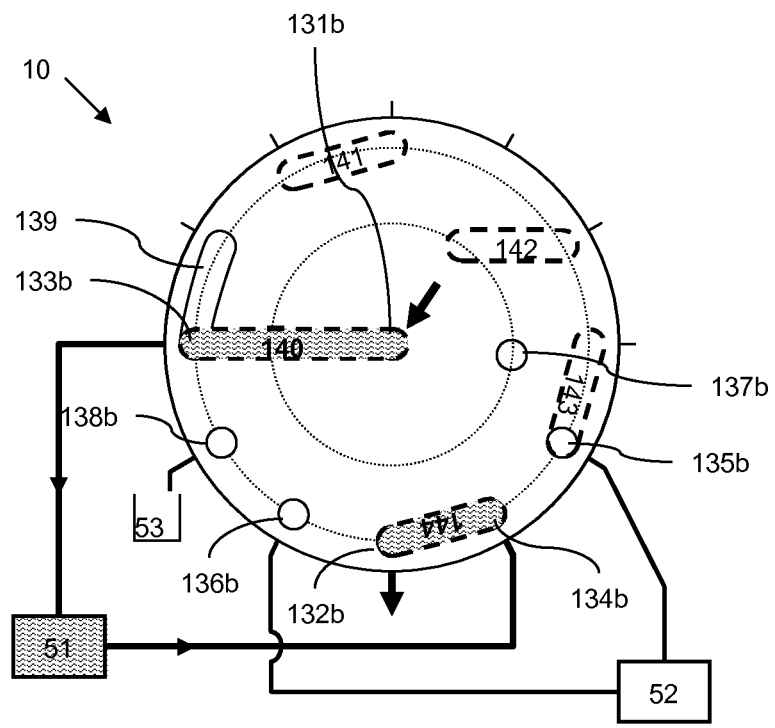

FIG. 10*b* shows the valve in a second rotor position wherein the interconnection paths in the rotor 12 interconnect the main inlet port 131*a* with the first component feed port 133*a* and the first component return port 134*a* with the main outlet port 132*a*. In this rotor position, the first component 51 is connected into the fluid flow, while the second component is bypassed. More specifically, the main inlet groove 140 interconnects the valve orifice 131*b* of the main inlet port and the valve orifice 133*b* of the first component feed port 133*a*, while the transfer groove 144 interconnects the valve orifice 134*b* of the first component return port 134*a* and the valve orifice 132*b* of the main outlet port 132*a*.

Figure 10C:
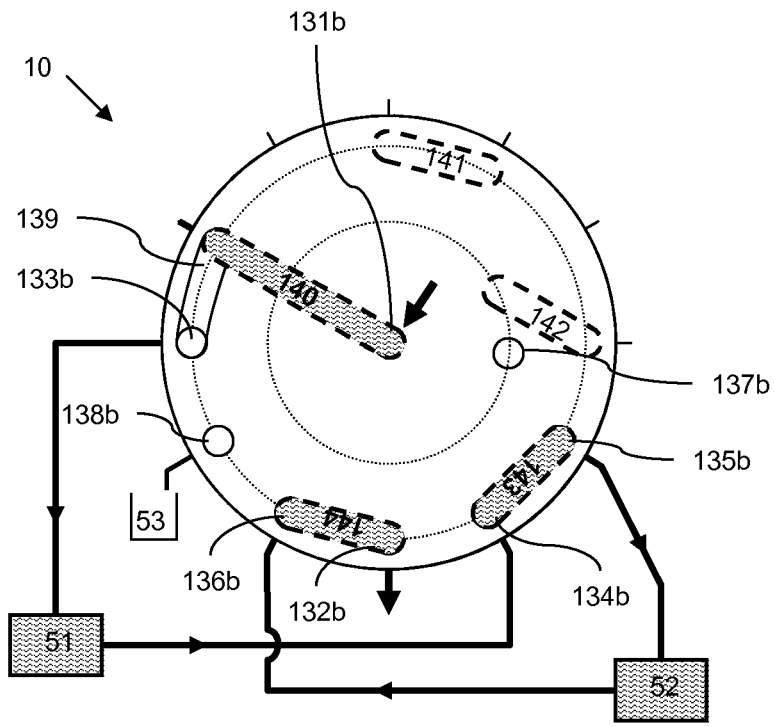
Figure 10D:
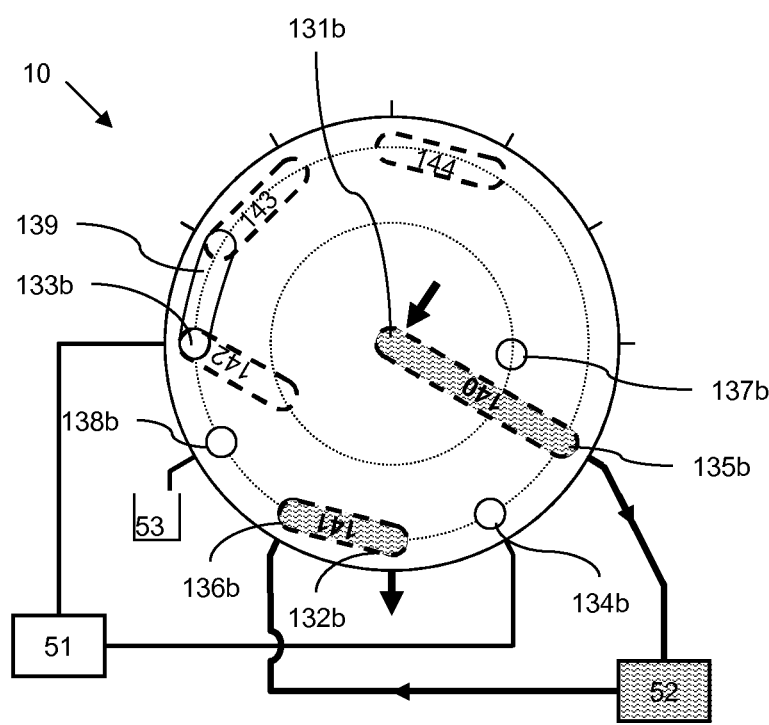
Figure 10E:
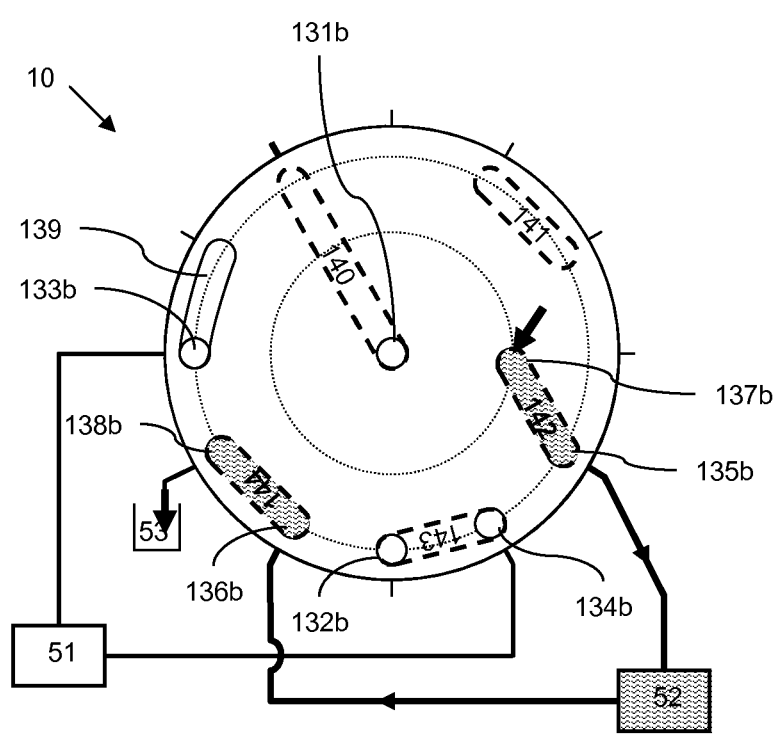

FIG. 10*c* shows the valve in a third rotor position wherein the interconnection paths in the rotor 12 interconnect the main inlet port 131*a* with the first component feed port 133*a*, the first component return port 134*a* with the second component feed port 135*a*, and the second component return port 136*a* with the main outlet port 132*a*. In this rotor position, both the first and second components 51 are connected into the fluid flow. More specifically, the main inlet groove 140 interconnects the valve orifice 131*b* of the main inlet port and the valve orifice 133*b* of the first component feed port 133*a* via the stator groove 139. The transfer groove 143 interconnects the valve orifice 134*b* of the first component return port 134*a* with the valve orifice 135*b* of the second component feed port 135*a*, while the transfer groove 144 interconnects the valve orifice 136*b* of the second component return port 136*a* with the valve orifice 132*b* of the main outlet port 132*a*.

FIG. 10*c* shows the valve in a fourth rotor position wherein the interconnection paths in the rotor 12 interconnect the main inlet port 131*a* with the second component feed port 135*a* and the second component return port 136*a* with the main outlet port 132*a*. In this rotor position, the second component 52 is connected into the fluid flow, while the first component 51 is bypassed. More specifically, the main inlet groove 140 interconnects the valve orifice 131*b* of the main inlet port 131*a* with the valve orifice 135*b* of the second component feed port 135*a*, while the transfer groove 141 interconnects the valve orifice 136*b* of the and the second component return port 136*a* with the valve orifice 132*b* of the main outlet port 132*a*.

FIG. 10*c* shows the valve in a fourth rotor position wherein the interconnection paths in the rotor 12 interconnect the secondary inlet port 137*a* with the second component feed port 135*a*, and the second component return port 136*a* with the secondary outlet port 138*a*. In this rotor position, the second component 52 is connected into a secondary fluid flow for calibration, flushing or the like, while the first component 51 is bypassed. In the disclosed embodiment, the fluid that is output from the secondary output is collected in a waste receptor 53. More specifically, the secondary inlet groove 142 interconnects the valve orifice 137*b* of the secondary inlet port 137*a* with the valve orifice 135*b* of the second component feed port 135*a*, while the transfer groove 144 interconnects the valve orifice 136*b* of the and the second component return port 136*a* with the valve orifice 138*b* of the secondary outlet port 138*a*.

As can be seen in FIGS. 10*a* to 10*e*, according to the disclosed embodiment, the first rotor position is selected as 0° and the equidistant spacing between adjacent valve orifices is 30°, then the second rotor position is at 90°, the third rotor position is at 120°, the fourth rotor position is at 300°, and the fifth rotor position is at 150°. As is pointed out above, that partition angle α and the relative positioning of the rotor positions may be selected in any way as long as the functional characteristics are achieved.

When the second component is a pH-sensor it is normally necessary to calibrate and/or flush the sensor at frequent intervals. The fifth rotary position then may be used for flushing the pH-sensor, whereby the pH-sensor can be calibrated and stored in a storage solution without having to be demounted from its holder.

Figure 11:
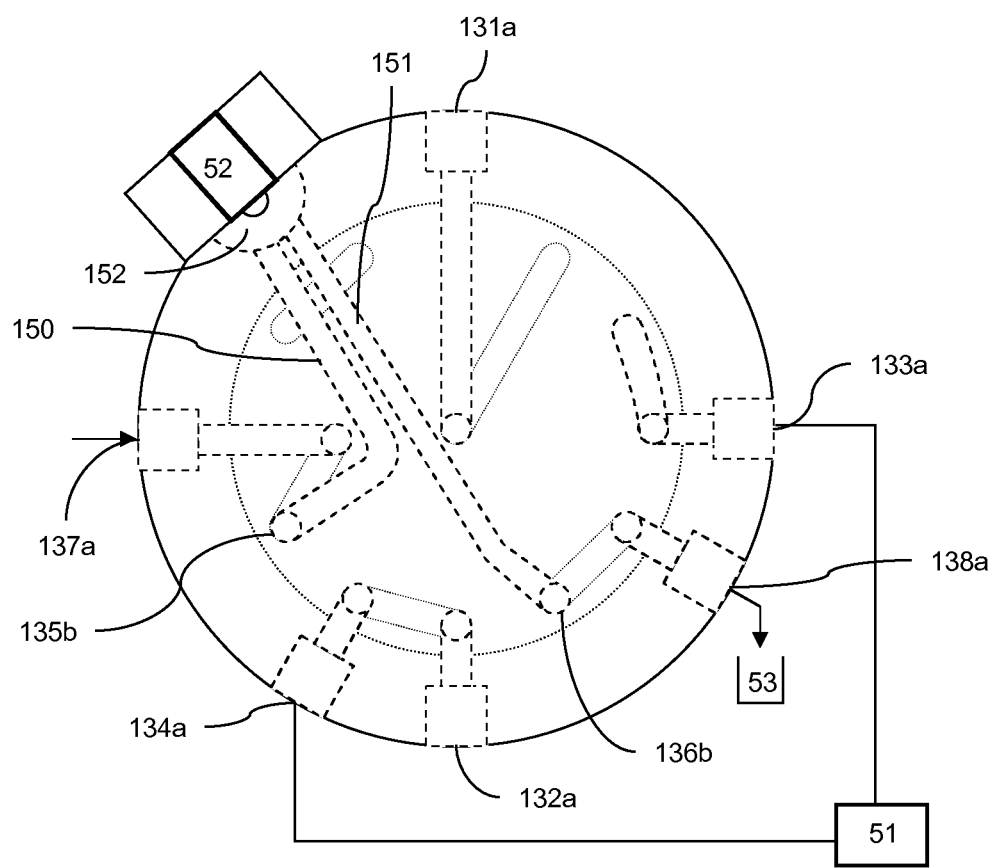
FIG. 11 is a schematic view of another embodiment of the invention in a second position.

FIG. 11 schematically shows an embodiment of a rotary valve 10 wherein the second component 52 in the form of a pH sensor is attached to the stator 11 in direct communication with the second component feed and return ports 135*a* and 136*a*. In this valve, internal interconnection paths 150 and 151 are formed in communication with a sensor cavity 152 wherein the pH sensor 52 is exposed to the fluid flow. In this way the connection of a pH sensor to the fluid path may be achieved with a minimum of fluid volume in the interconnection paths, compared to when the pH sensor is connected by means of tubing.

As described above the exact position of the orifices need not to be according to the embodiment described above. What is important for the invention is that the different grooves reaches the specific orifices that should be reached in each rotation position described above.

What is claimed is:

1. A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more interconnection paths for selective fluidic interconnection of said valve orifices with respect to the rotor position, wherein
    the plurality of connection ports include, a main inlet port, a main outlet port, a first component feed port, a first component return port, a second component feed port, a second component return port, and wherein
    the interconnection paths in the rotor are arranged to:
        in a first rotor position interconnect the main inlet port with the main outlet port,
        in a second rotor position interconnect the main inlet port with the first component feed port and the first component return port with the main outlet port,
        in a third rotor position interconnect the main inlet port with the first component feed port, the first component return port with the second component feed port, and the second component return port with the main outlet port, and
        in a fourth rotor position interconnect the main inlet port with the second component feed port and the second component return port with the main outlet port.

2. The rotary valve of claim 1, wherein the valve orifice of the main inlet port is arranged concentric with the rotational axis, the valve orifices of the main outlet port and the first and second component feed ports are angularly distributed at a distance R from the rotational axis, and that the rotor comprises a main inlet interconnection path between the valve orifice of the main inlet port and one point at distance R from the rotational axis.

3. The rotary valve of claim 2, wherein the first component feed port is in fluidic contact with the main inlet interconnection path of the rotor at both the second and third rotor position via a stator interconnection channel extending the valve orifice of the first component feed port.

4. The rotary valve of claim 2, wherein the valve orifices of the first and second component return ports are angularly distributed at distance R from the rotational axis, and the two or more transfer interconnection paths provide for selective pair wise interconnection of the valve orifices arranged at distance R from the rotational axis.

5. The rotary valve of claim 4, wherein the valve orifices of the main outlet port, the second component feed port and the first and second component return ports are equidistantly distributed, and that each transfer interconnection path is arranged to interconnect adjacent valve orifices.

6. The rotary valve of claim 1, wherein the stator further comprises a secondary inlet port and a secondary outlet port, and wherein the interconnection paths in the rotor are arranged to:
in a fifth rotor position interconnect the secondary inlet port with the second component feed port, and the second component return port with the secondary outlet port.

7. The rotary valve of claim 6, wherein the valve orifice of the secondary inlet port is arranged at distance R2 from the rotational axis, R≠R2, and the rotor comprises a secondary source interconnection path that is arranged to interconnect the valve orifices of the secondary inlet and the second component feed port when the rotor is in the fifth rotor position, whereas one of the transfer interconnection paths is arranged to interconnect the valve orifices of the second component feed port and the secondary outlet port.

8. The rotary valve of claim 6, wherein the first rotor position is selected as 0° and the equidistant spacing between adjacent valve orifices is 30°, then the second rotor position is at 90°, the third rotor position is at 120°, the fourth rotor position is at 300°, and the fifth rotor position is at 150°.

9. An analytical instrument comprising the rotary valve of claim 1.

* * * * *